(12) United States Patent
Cathey

(10) Patent No.: US 9,066,743 B1
(45) Date of Patent: Jun. 30, 2015

(54) SUPPORT SYSTEM FOR SURGICAL INSTRUMENT

(71) Applicant: Keith Cathey, Tulsa, OK (US)

(72) Inventor: Keith Cathey, Tulsa, OK (US)

(*) Notice: Subject to any disclaimer, the term of this patent is extended or adjusted under 35 U.S.C. 154(b) by 174 days.

(21) Appl. No.: 13/972,150

(22) Filed: Aug. 21, 2013

Related U.S. Application Data

(63) Continuation-in-part of application No. 13/164,604, filed on Jun. 20, 2011, now abandoned.

(51) Int. Cl.
*A61B 1/32* (2006.01)
*A61B 19/00* (2006.01)
*A61B 17/02* (2006.01)
*A61B 17/42* (2006.01)

(52) U.S. Cl.
CPC .............. *A61B 19/26* (2013.01); *A61B 17/02* (2013.01); *A61B 17/42* (2013.01)

(58) Field of Classification Search
CPC .. A61B 17/42; A61B 19/26; A61B 2019/263; A61B 2019/264
See application file for complete search history.

(56) References Cited

U.S. PATENT DOCUMENTS

| 7,201,747 | B2 | 4/2007 | Edoga et al. |
| 7,744,530 | B2 | 6/2010 | Person |
| 2003/0065289 | A1 | 4/2003 | Clayton |
| 2003/0187334 | A1 | 10/2003 | Biswas |
| 2007/0289597 | A1 | 12/2007 | Masella et al. |
| 2012/0323082 | A1 | 12/2012 | Cathey |

*Primary Examiner* — Andrew Yang
*Assistant Examiner* — Olivia C Chang
(74) *Attorney, Agent, or Firm* — Molly D. McKay

(57) ABSTRACT

A holding device for a surgical instrument that includes a central instrument holding plate with a channel for removably receiving the neck of a weighted speculum, patient attachment straps extending from the holding plate and configured to surround a patient's thighs as a means for securing the holding plate to a patient's vaginal area, and instrument fasteners attached to the holding plate for releasably holding the weighted speculum when the weighted speculum is in use. The instrument fasteners are cooperating flexible arms that are configured to releasably hold the speculum within the channel of the holding plate. The channel sized and shaped so that it does not interfere with the functioning of the weighted speculum.

4 Claims, 7 Drawing Sheets

SUPPORT SYSTEM FOR SURGICAL INSTRUMENT

CROSS-REFERENCE TO RELATED APPLICATIONS

The present application is a continuation in part of U.S. patent application Ser. No. 13/164,604 for Support System for Surgical Instrument that was filed on Jun. 20, 2011.

BACKGROUND OF THE INVENTION

1. Field of the Invention

The present invention generally relates to a system for holding a surgical instrument in position on a patient during a surgical procedure. More specifically, the present invention is a support system for holding a weighted speculum on a patient during a surgical procedure so that the weighted speculum remains in position and does not fall to the ground.

2. Description of the Related Art

During some surgical procedures it may be necessary to support a device the holds a portion of a patient's anatomy in a particular fixed position during the procedure. For example, in gynecological procedures a weighted speculum may be employed to maintain an opening that allows a surgeon to gain access to various anatomical elements within the patient's body. The weighted speculum may hold vaginal tissue in a separated and open state. Because of its weight, (approximately 5 pounds) gravitational force may cause the speculum to naturally maintain the tissue into the desired open state. The weight of the speculum may also result in a tendency for the speculum to slip out of the patient.

If a weighted speculum were to slip out of a patient, the speculum would, at a minimum, require re-sterilization, or in a worse case, a falling weighted speculum may drop and strike a surgeon or other operating room staff member and cause personal injury. Thus, it is normal practice in such gynecological procedures to assign a surgical assistant the task of holding the speculum to assure that it does not slip out of the patient.

As can be seen, there is a need for a system of maintaining an instrument such as a speculum securely in position without a need for assigning a surgical assistant the task of holding the instrument in position.

SUMMARY OF THE INVENTION

In one aspect of the present invention, a holding device for a surgical instrument may comprise: a central instrument holding plate; patient attachment straps extending from the holding plate; and at least one instrument fastener attached to the holding plate.

In another aspect of the present invention, a device for holding a weighted speculum in position on a patient may comprise: a central holding plate for the speculum; patient-attachment straps extending from the holding plate and configured to surround thighs of the patient; and at least one fastener attached to the holding plate configured to hold the speculum.

In still another aspect of the present invention, a method of performing a gynecological procedure on a patient may comprise the steps of providing for placement of at least one fastener for a weighted speculum in a region adjacent a vaginal opening of the patient and providing for flexible and removable attachment of the weighted speculum to the fastener.

These and other features, aspects and advantages of the present invention will become better understood with reference to the following drawings, description and claims.

DETAILED DESCRIPTION OF THE PREFERRED EMBODIMENT

Figure 1:
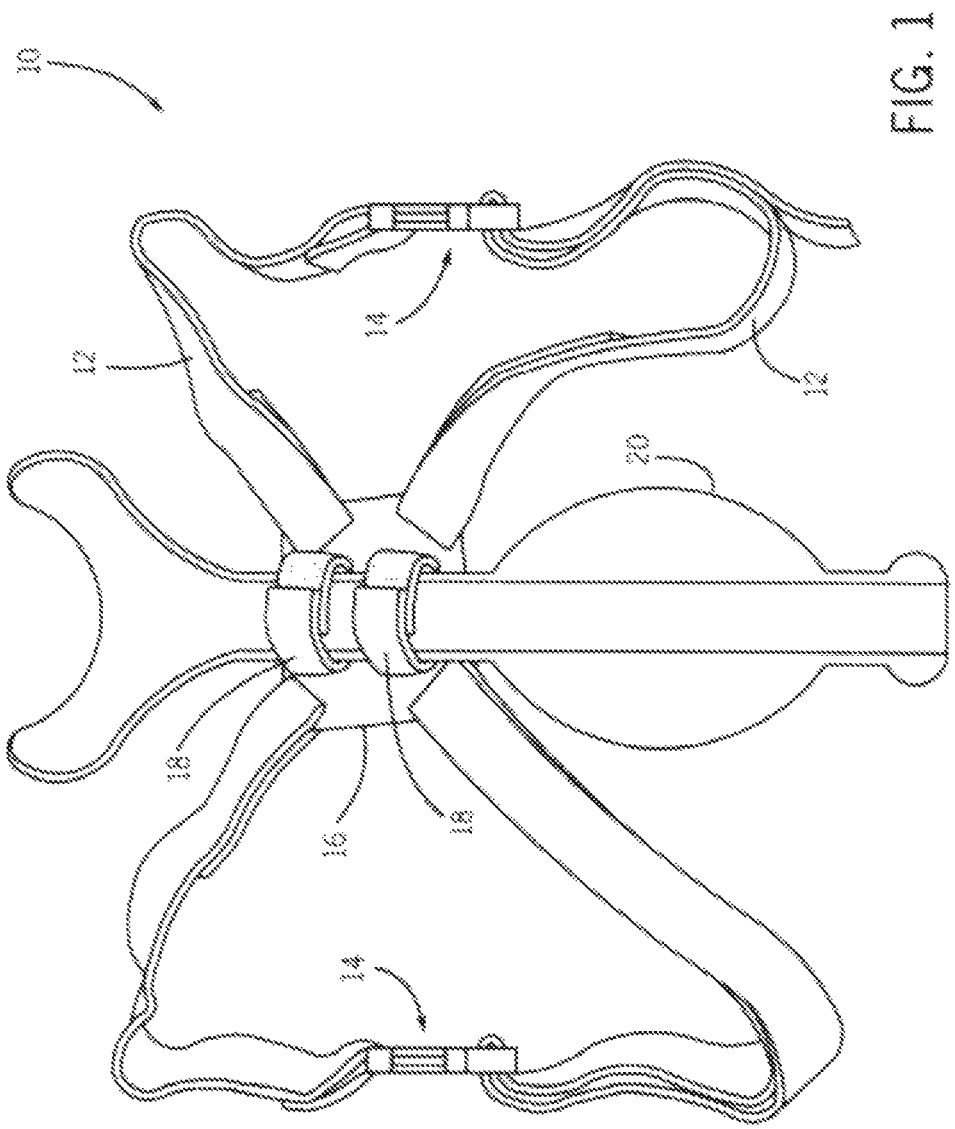
FIG. 1 is a perspective view of a holding device for a weighted speculum that is constructed in accordance with one embodiment of the invention and show with a weighted speculum secured thereto with straps that fasten together with hook and loop fasteners.
Figure 2:
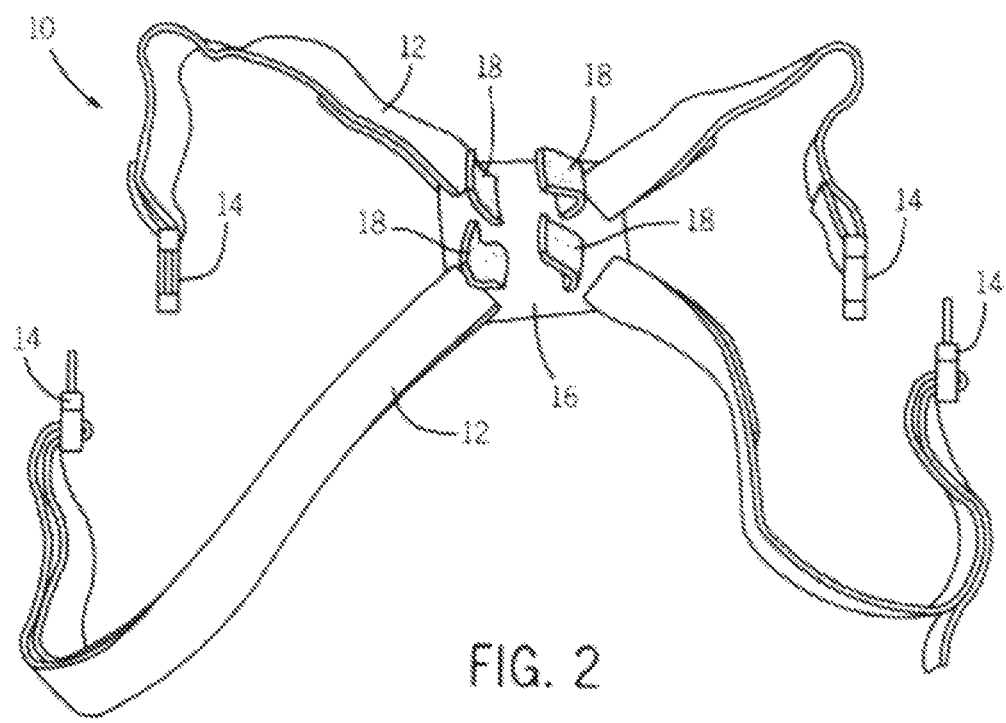
FIG. 2 is a perspective view of the holding device for a weighted speculum shown with the weighted speculum removed.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features.

Broadly, embodiments of the present invention generally provide a holding system in which a holding device may be secured to a patient and an instrument may be attached to the device and held securely in position at a desired location relative to the patient.

Referring now to FIGS. 1-4, it may be seen that an exemplary embodiment of a holding device 10 may be configured to hold an instrument 20, for example a weighted speculum, in position on a patient. The holding device 10 may comprise patient-attachment straps 12, a central holding plate 16 and instrument fasteners 18.

Advantageously, the holding device 10 may be brought into a surgical setting as a pre-packed sterile unit. The patient-attachment straps 12 may be flexible or elastomeric fabric. The patient-attachment straps 12 may be adjustable in length and may be provided with buckles 14. The central holding plate 16 may be comprised of semi-rigid plastic foam without any sharp edges. All materials used in construction of the holding device 10 should be tolerant of being sterilized.

Figure 3:
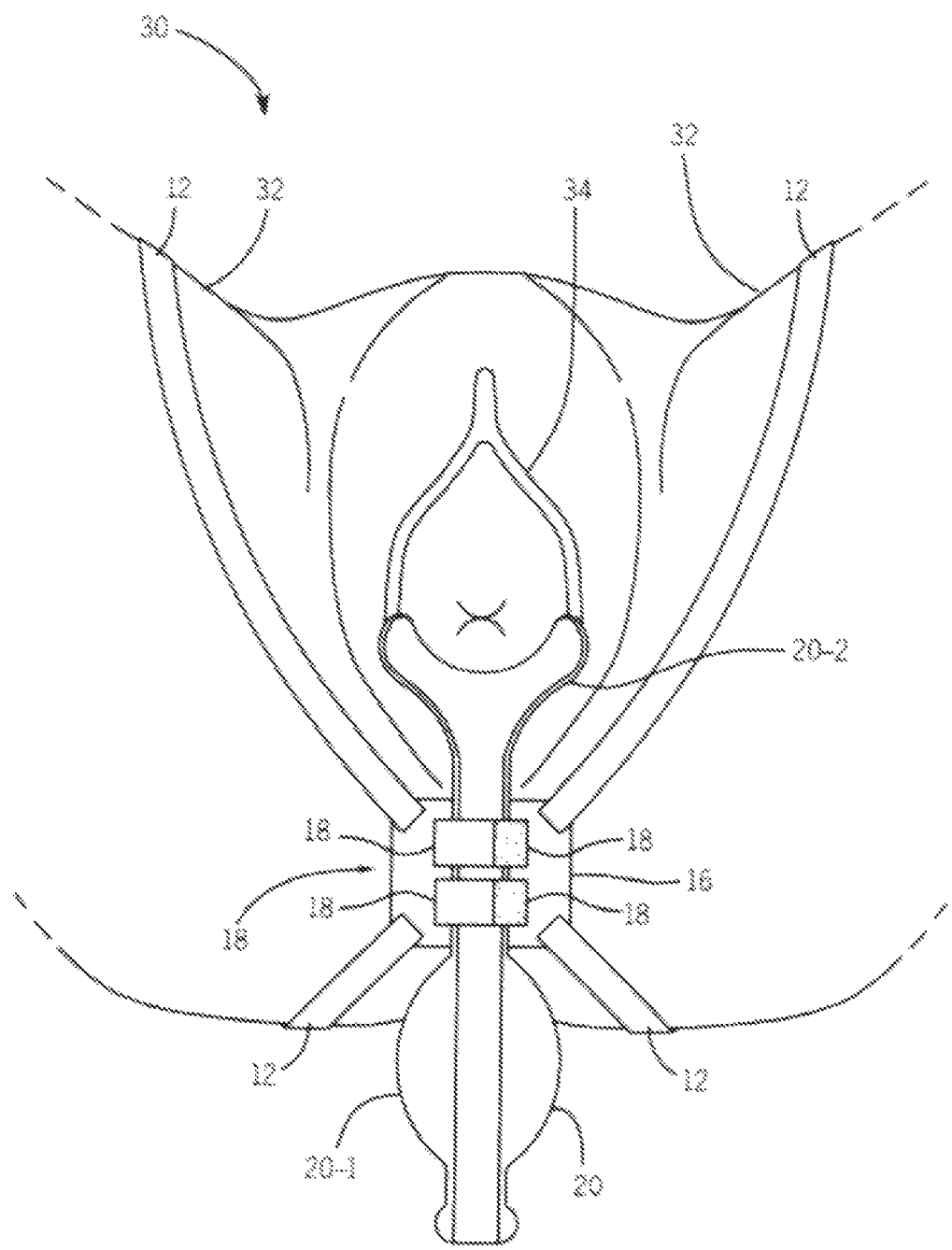
FIG. 3 is a perspective view of the holding device of FIGS. 1 and 2 shown in position on a patient holding a weighted speculum in place.

Referring now particularly to FIG. 3, it may be seen that in an exemplary application of the holding device 10, the patient-attachment straps 12 may be placed around thighs 32 of a patient 30. The patient-attachment straps 12 may be adjusted in length so that the central holding plate 16 may be held securely against the patient 30. The surgical instrument 20 may be positioned as desired in the patient 34 and the instrument fasteners 18 may be secured around the instrument 20.

In the exemplary case of the instrument 20 being a weighted speculum, the instrument 20 may be positioned to hold open the patient's vagina. A weighted speculum 20 is constructed with a weighted end 20-1. Gravitational force on the weighted end 20-1 may cause an opposite contact portion 20-2 of the instrument 20 to exert a downward force on the vaginal opening 34 of the patient 30. This downward force may be useful in maintaining an open region through which a surgeon may perform a procedure.

It may be noted that the instrument fasteners 18 may be configured so that they may be engaged with the instrument 20 in a manner that does not preclude the desirable effects of the weighted end 20-1 on the functionality of the instrument 20. In other words, the fasteners 18 may be constructed so that they may be attached to the instrument 20 with enough flexibility as to allow the weighted end 20-1 to continue exerting desired downward force on the contact portion 20-2 as described above.

Advantageously, the instrument fasteners 18 may be constructed so that their engagement force with the instrument 20 may be adjusted as desired to allow for full functionality of the instrument 20. For example, the fasteners may comprise hook and loop material (e.g., Velcro®). Alternatively, the fasteners 18 may comprise adjustable straps (not shown) that fasten together with snaps or buckles (not shown).

Figure 4:
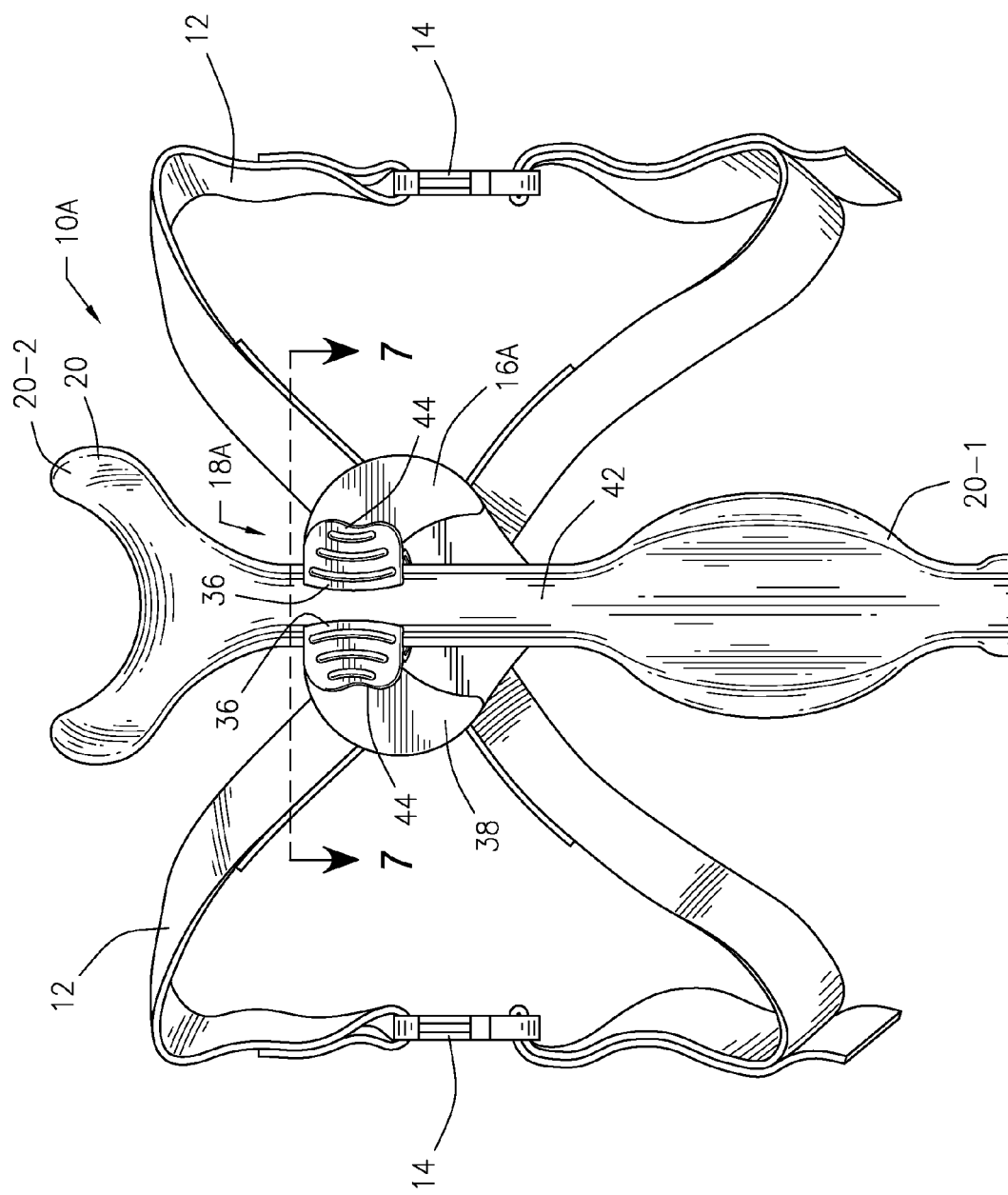
FIG. 4 is a perspective view of an alternate holding device for a weighted speculum that is construct in accordance with a preferred embodiment of the present invention, shown with a weighted speculum secured thereto with opposing clips designed to receive the neck of the weighted speculum there between, FIG. 5 is a perspective view of the alternate holding device of FIG. 4 shown with the weighted speculum removed.
Figure 5:
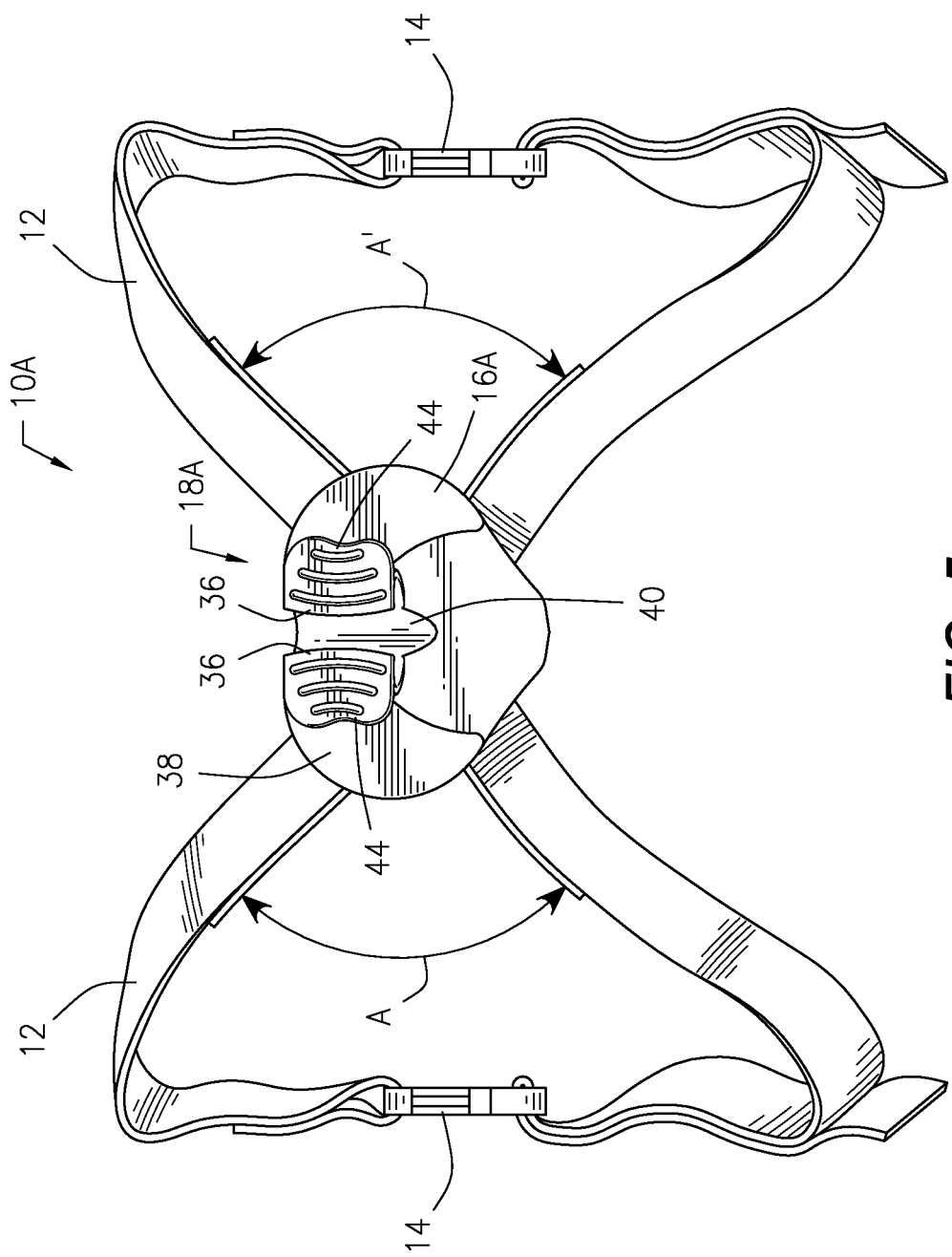
Figure 6:
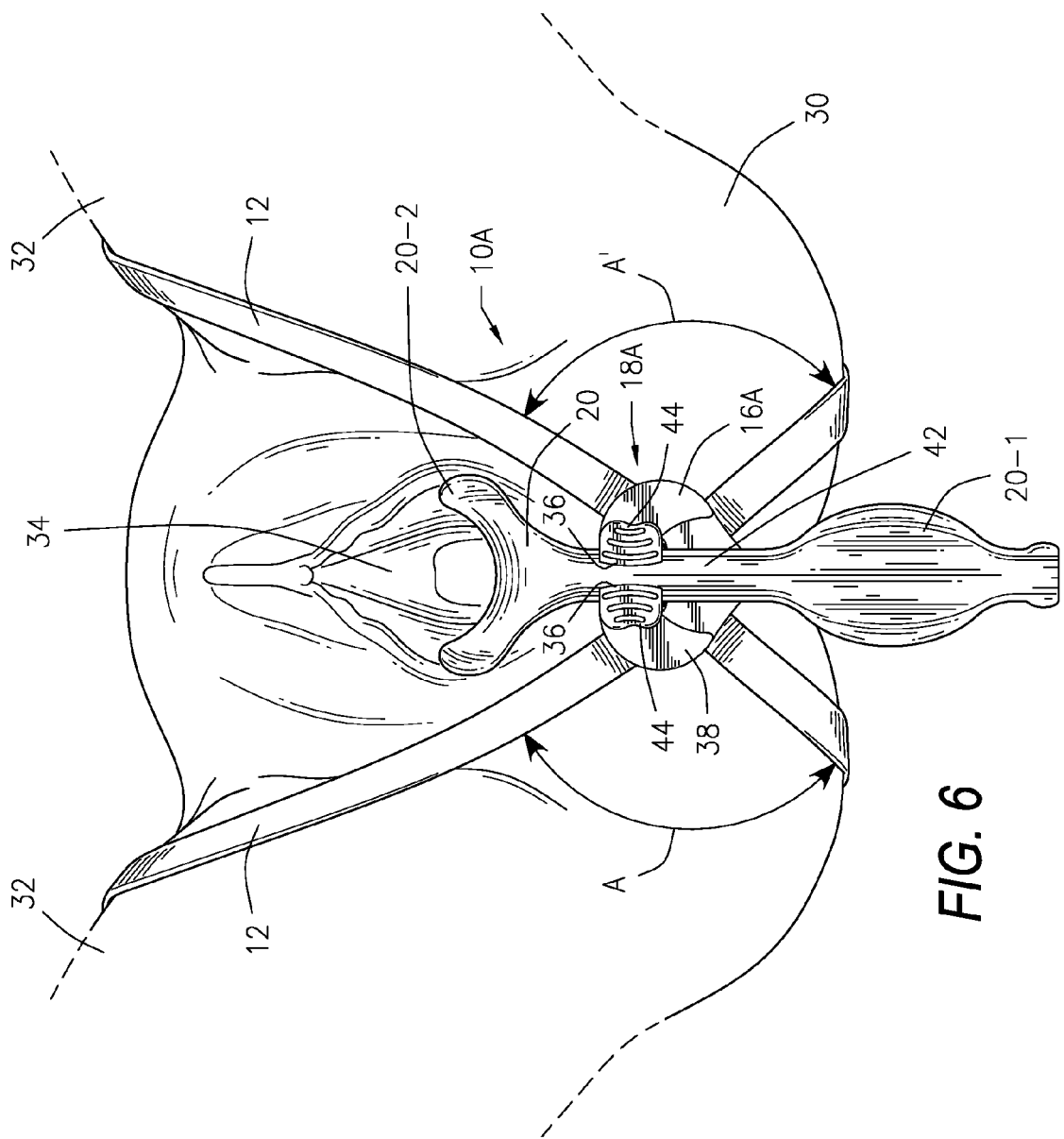
FIG. 6 is a perspective view of the alternate holding device of FIGS. 4 and 5 shown in position on a patient holding a weighted speculum in place.

Referring now to FIGS. 4-8, there is illustrated an alternate holding device 10A that is constructed in accordance with a preferred embodiment of the present invention. The alternate holding device 10A differs from the holding device 10 described previously in that the device is provided with an alternate central holding plate 16A that includes opposing arms 36 of an alternate clasp instrument fastener 18A located on the front side 38 of the alternate central holding plate 16A. The opposing arms 36 are biased inwardly so that the arms 36 form a channel 40 there between such that the channel 40 is of a shape and size to receive therein and to hold the neck 42 of a weighted speculum 20, as illustrated in FIGS. 4 and 6.

Figure 7:
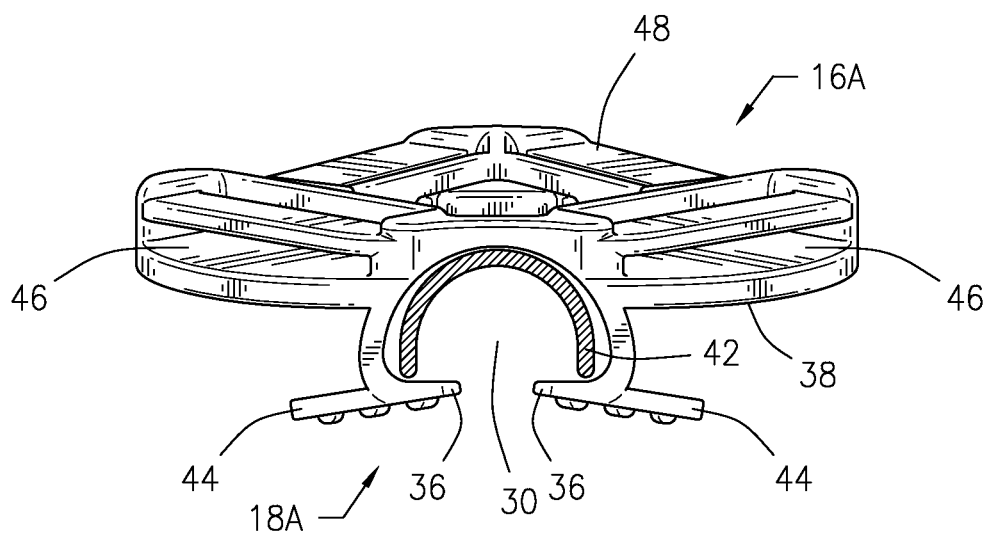
FIG. 7 is a cross sectional view of the alternate central holding plate of the alternate holding device taken along line 7-7 of FIG. 4.
Figure 8:
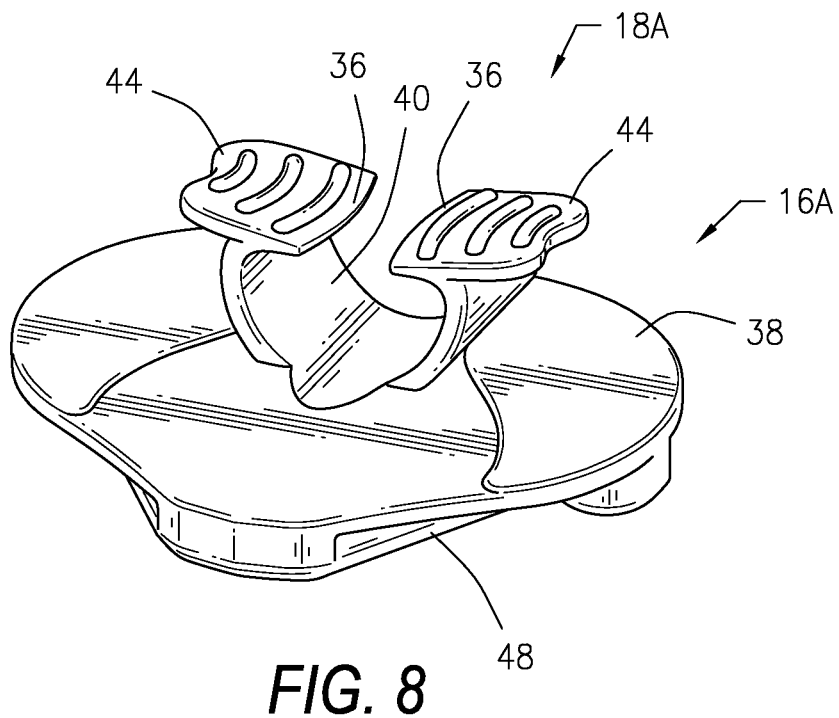
FIG. 8 is a perspective view of the alternate central holding plate of FIG. 7 shown with the weighted speculum removed.

Referring now to FIGS. 5, 7 and 8, each of the opposing arms 36 is provided with a thumb lever 44 that can be depressed by pressing against it to cause the arms 36 to flex outward. As the arms 36 flex outward, this opens up the channel 40 so that the neck 42 of the weighted speculum 20 can be inserted into or removed from the channel 40 to alternately secure the weighted speculum 20 to the alternate central holding plate 16A and to release the weighted speculum 20 from the alternate central holding plate 16A.

The alternate central holding plate 16A is provided with strap openings 46 on its opposite rear side 48 by which the patient-attachment straps 12 attach to the alternate central holding plate 16A as a means of attaching the alternate central holding plate 16A to the thighs 32 of the patient 30. The strap openings 46 are oriented in such a manner that the two cooperating patient-attachment straps 12 that extend outward from each side of the alternate central holding plate 16A are properly oriented for use at approximately 90 degree angles A and A' from each other, as shown in FIGS. 5 and 6.

While the invention has been described with a certain degree of particularity, it is manifest that many changes may be made in the details of construction and the arrangement of components without departing from the spirit and scope of this disclosure. It is understood that the invention is not limited to the embodiments set forth herein for the purposes of exemplification, but is to be limited only by the scope of the attached claim or claims, including the full range of equivalency to which each element thereof is entitled.

What is claimed is:

1. A support system for surgical instrument comprising:
   a semi-rigid central instrument holding plate for use against the vaginal area of a patient, said instrument holding plate provided with a channel therein that is slightly larger than the neck of a weighted speculum so that a weighted speculum can be held within the channel without affected the functioning of the weighted speculum,
   a first patient attachment strap and a second patient attachment strap extending from a first side of the holding plate, fasteners for removably attaching distal ends of the first and second patient attachment straps together to secure the first side of the holding plate to a patient's thigh located on the first side of the holding plate,
   a third patient attachment strap and a fourth patient attachment strap extending from an opposite second side of the holding plate, fasteners for removably attaching distal ends of the third and fourth patient attachment straps together to secure the second side of the holding plate to a patient's thigh located on the second side of the holding plate,
   at least one clasp instrument fastener attached to the holding plate as a means for removably securing a weighted speculum within the channel provided in the holding plate when the weighted speculum is in use,
   each instrument fastener configured for flexible engagement with the neck of a weighted speculum,
   each instrument fastener having two cooperating opposing arms that flex outward relative to each other to allow the neck of a weighted speculum to be admitted into and removed from the chamber provided in the holding plate,
   a thumb lever provided on each opposing arm as a means for flexing the arms outward relative to each other.

2. The holding device of claim 1 wherein the patient-attachment straps are comprised of flexible fabric.

3. The holding device of claim 1 wherein the fasteners for removably attaching distal ends of the first and second patient attachment straps together patient attachment straps include means for adjusting the length of the straps.

4. The holding device of claim 1 wherein the first and second patient attachment straps are oriented at approximately a right angle to each other, and wherein the third and fourth patient attachment straps are oriented at approximately a right angle to each other.

* * * * *